United States Patent [19]

Rietschel et al.

[11] Patent Number: 4,868,124
[45] Date of Patent: Sep. 19, 1989

[54] VAPOR STERILIZABLE BIOREACTOR

[75] Inventors: Wolfgang Rietschel, Söhrewald; Reinhard Kiel, Melsungen; Wolfgang Kahlert, Körle; Winfried Kuhlmann, Melsungen, all of Fed. Rep. of Germany

[73] Assignee: B. Braun Melsungen AG, Melsungen, Fed. Rep. of Germany

[21] Appl. No.: 195,726

[22] Filed: May 18, 1988

[30] Foreign Application Priority Data

Jun. 16, 1987 [DE] Fed. Rep. of Germany ....... 3720049

[51] Int. Cl.⁴ .......................... C12M 1/12; F16K 3/30
[52] U.S. Cl. ..................... 435/311; 435/313;
435/315; 435/316; 137/240; 137/241; 137/588;
137/590; 422/103
[58] Field of Search ............... 435/311, 313, 315, 316;
137/240, 241, 587, 588, 592, 590, 862, 874;
251/343, 353; 422/103, 26, 27; 210/541

[56] References Cited

U.S. PATENT DOCUMENTS

| 889,952 | 6/1908 | McGinley et al. | 251/353 X |
| 901,741 | 10/1908 | Reed | 137/240 X |
| 1,432,259 | 10/1922 | Richards, Jr. | 137/590 |
| 3,203,665 | 8/1965 | Grant et al. | 251/353 X |
| 4,119,110 | 10/1978 | Stone | 137/240 X |
| 4,426,450 | 1/1984 | Donofrio | 435/313 X |
| 4,742,851 | 5/1988 | Lundblade | 251/353 X |

FOREIGN PATENT DOCUMENTS 3539798 5/1987 Fed. Rep. of Germany ...... 137/592

Primary Examiner—Robert E. Garrett
Assistant Examiner—Carl D. Price
Attorney, Agent, or Firm—Spensley Horn Jubas & Lubitz

[57] ABSTRACT

An immersion tube dipping into a fluid is connected via a valve and via a 3/2-valve to a condensate line and to a working line. In the sterilization position, vapor flows through the valve and through the 3/2-way valve and the valve is in a position which is open to the head space of the vessel and to the tube. As a result, all of the inner space of the vessel is exposed to the same pressure. In the operating position, the valve connects the duct only to the interior of the immersion tube, while the connection to the head space is blocked. All components connected to the line are sterilized by vapor.

8 Claims, 1 Drawing Sheet

VAPOR STERILIZABLE BIOREACTOR

BACKGROUND OF THE INVENTION

1. Field of the Invention

The invention relates to a bioreactor and in particular to a bioreacter containing a means for the vapor sterilization of the inner space of the reactor vessel and of the tubes extending beneath the fluid level of said vessel.

2. Description of Related Art

Bioreactors are used for the culture and growth of biological substances such as cells and enzymes. Their operation requires absolute freedom from contamination. Bioreactors are made of vapor-sterilizable materials; e.g., special steel. To eliminate undesired germs, sterilization is typically performed by vapor which is either formed at a temperature of about 121° C in the vessel or which is introduced into the vessel under pressure. The function of the vapor is to sterilize not only the inner space of the vessel, but also the interior of the tubing inside the vessel and, in particular, the immersion tubes. It is relatively simple to sterilize an empty bioreactor, while difficulties arise if a fluid; e.g., a nutrient broth, is contained in the bioreacter because, due to vapor pressure, fluid is driven out through the tubes to be sterilized, or, if the tubes are closed, the air space within them is not sterilized by the vapor.

It has been known to provide a separate vapor connection at the vessel for the vapor sterilization of a bioreactor. However, in such a case, a higher expenditure is involved with the vessel and the vapor is introduced into the fluid present in the vessel. Very often, the introduction of vapor into the fluid is undesired.

It has been further known to provide, in the wall of the head space of the vessel, a diaphragm which is pierced by a hollow needle to introduce vapor (it being necessary to previously sterilize the needle by a flame). However, contamination due to the introduction of the needle into the interior of the vessel cannot be entirely excluded. The tubes, filters and other means to be connected must be previously sterilized separately.

According to DE-OS 35 39 798, there has been known a valve for sterilizing a bioreactor which includes in its cover the valve chamber. A part of the valve chamber which projects into the head space of the reactor is provided with openings. A slide is displaceable in a bore of the valve chamber. The external end of the slide may be joined to a vapor line. The inner end of the slide is provided with two axially spaced seals. In the operating position of the valve, when the slide is lowered, the channel of the slide is connected to a tube extending as far as to the bottom of the vessel. In the sterilizing position, when the slide is lifted, vapor fed through the channel of the slide flows through the free opening of the valve chamber into the head space of the vessel. It is a disadvantage of said valve that, in the sterilizing position, the slide section between the two seals is not contacted by vapor and, accordingly, remains unsterilized. In the operating position, said section communicates through the openings with the sterilized region of the vessel, and a contamination of the vessel content may occur.

It is an object of the present invention to provide a bioreacter in which, during sterilization, all of the areas which communicate with the vessel region in the operating phase are sterilized, thus safely inhibiting any contamination.

SUMMARY OF THE INVENTION

In accordance with the present invention, these and other objectives are achieved by providing a bioreactor in which, during the sterilization phase, vapor flows through the enlarged bore of the valve chamber and around the lower end region of the slide to accordingly sterilize it. Said vapor also gets into the bore over a certain length thereof, thus sterilizing the lower region of the bore wall. Hence, all elements which, during the operating phase, may communicate with the opening of the valve chamber and with the sterilized region of the vessel are sterilizable. The duct connected to the valve and the accessory connected to the line are sterilized concomitantly and need not be subjected to a separate sterilization.

BRIEF DESCRIPTION OF THE DRAWINGS

A detailed description of a preferred embodiment of the invention will be made with reference to the accompanying drawings, wherein like numerals designate corresponding parts in the several figures.

DESCRIPTION OF THE PREFERRED EMBODIMENT

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
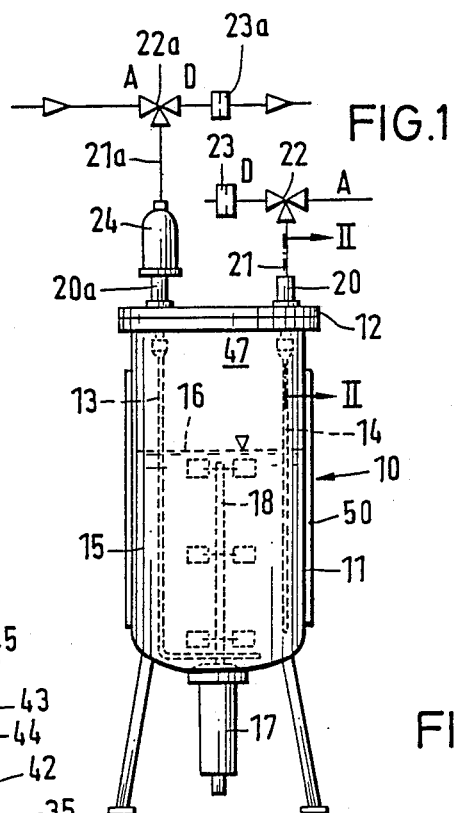
FIG. 1 is a schematic view of a preferred embodiment of a bioreactor and lines connected hereto.

As illustrated in FIG. 1, a preferred embodiment of the bioreactor 10 comprises a vessel 11 made of special steel and sealed hermetically. The vessel 11 includes a heating means 50 which, in the instant case, is mounted externally, but could also be accommodated inside the vessel. The vessel 11 is closed by a sealingly applied cover 12 from which extend downwardly immersion tubes 13 and 14. Tube 13 is a gassing tube through which gas may be introduced from below into the liquid 15 (whose level in the vessel 11 is designated by the numeral 16). Tube 14 is a supply or removal tube for the delivery or removal of liquid. Other connections may additionally be provided at the cover 12 (such as pressure connections as well as passages for measuring probes, etc.), but these additional connections are not shown in order to provide a better survey. An agitator drive 17 is provided under the bottom of the vessel 11 to drive an agitator 18 arranged in the lower region of the vessel.

Inside the vessel 11, the tube 14 is connected to the vapor-sterilizable valve 20 which is secured to the cover 12 and sealingly guided through the cover 12. Outside the cover 12, the valve 20 is joined to a duct 21 which is connected to the 3/2-way valve 22 which is provided with two additional connections D and A. Connection D is joined via a pressure-reducing throttle member 23 to a discharge, while operating connection A extends to a supply line or discharge line.

According to FIG. 1, the tube 13 is also connected to a valve 20a corresponding to the valve 20, said valve 20a being connected via a filter 24 and a duct 21a to the 3/2-way valve 22a. Connection D of the 3/2-way valve 22a is connected to a discharge via a pressure-reducing throttle member 23a, while the operating connection A is connected to a gassing line.

Normally, the sterilization of the bioreactor requires one valve 20 or 20a only at one of the tubes 13 or 14 dipping into the liquid. However, to better explain matters, two tubes are provided with such a valve in FIG. 1. In reality, it may be adequate to provide each tube 13 and 14 with a valve 20a or 20.

The following description of the valve is directed to valve 20. The design of valve 20a is exactly the same.

Valve 20 comprises an elongated, tubular valve chamber 25 which is mounted from the outside into a seat of the cover 12 and is supported by a collar 26 at an annular shoulder in the cover passage. Beneath the collar 26 there is provided, in an annular groove of the valve chamber 25, a seal 27 which ensures sealing between the valve chamber 25 and the cover 12.

Closely beneath the cover 12, the valve chamber 25 has lateral openings 28 under which a cylindrical seat 29 is provided. Below the seat 29 there is a tube connection 30 with a thread to which the head 31 of the tube 14 is fixed. The head 31 is sealed with a seal 32 for the seat 29 so that the space enclosed by the seat 29 sealingly communicates with the interior of tube 14.

The valve chamber 25 is secured to the cover 12 by means of a nut 33 externally applied against the cover 12 and encompassing the cylindrical body of the valve chamber. By an external thread, the nut 33 is screwed into an internal thread of the cover passage. By this means, the nut 33 urges the collar 26 against the annular shoulder of the cover 12.

A substantially cylindrical slide 35 is arranged to be longitudinally displaceable in a substantially vertical, longitudinal bore 34 of the valve chamber 25. Near the lower end of the slide 35 there is a first seal 36 and, in spaced relationship thereabove, there is a second seal 37. An annular groove 38 is provided between the seals 36 and 37. The diameter of the upper end 39 of the slide 35 is larger than the diameter of the region in which seals 36 and 37 are positioned. The bore of the valve chamber 25 is correspondingly enlarged over the length into which the thicker region 39 extends. At the lower end of the thicker region 39, there is a radially projecting guide pin 40 extending into a longitudinal groove 41 of the valve chamber 25. The guide pin 40 functions to protect the slide 35 against twisting relative to the valve chamber 25 and limits the axial displacement area of the slide 35.

An axial bore 42 extends through the slide 35 over its total length. The upper end of the slide 35 is provided with a connector 43 with a thread 44 and a seal 45 to join a tube or other device (such as, for example, the filter 24 illustrated in FIG. 1).

Figure 2:
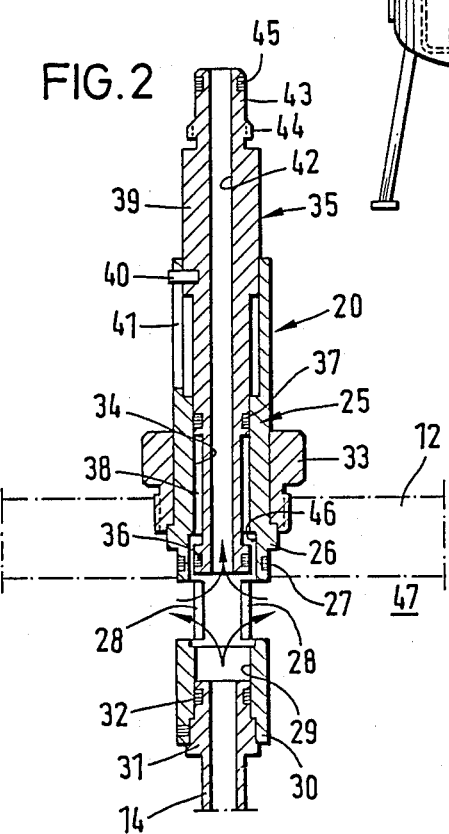
FIG. 2 is a longitudinal cross section of a preferred embodiment of the valve along the line II—II of FIG. 1, in the first valve position; i.e., in the "sterilization" mode.

In the upper position of slide 35 shown in FIG. 2, the first seal 36 is positioned at the lower end of the slide 35 within the range of an enlargement 46 of the bore 34 so that the annular groove 38 communicates via the enlargement 46 and the openings 28 with the head space 47 of the vessel 11.

FIG. 2 shows the valve 20 in the "sterilization" position or mode. In this mode, the slide 35 occupies its upper end position. The second seal 37 cooperates with the bore 34 to ensure a seal between the slide 35 and the valve chamber 25 in each of the two positions of the slide 35 (as well as in intermediate positions). In the sterilization position of the valve 20, the 3/2 way valve 22 is switched to position D. The heating means 50 heats the fluid to form vapor. The vapor flows from the head space 47 through the openings 28 into the channel 42 of the slide 35. By this means, all elements connected to the duct 21, including the multiway-valve 22, the valve 20 and the tube 14 are sterilized by vapor. Further, the portion of the bore 34 situated beneath the second seal 37 and the region of the slide 35 beneath the seal 37 are sterilized as well.

Figure 3:
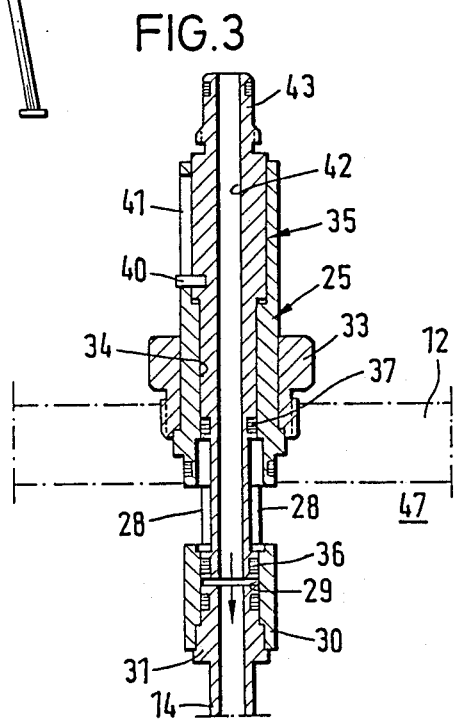
FIG. 3 is a view similar to FIG. 2 showing the second valve position which is the operative mode.

In the working position shown in FIG. 3, the slide 35 is moved into the lower position. In this position, the end of the slide 35 containing the first seal 36 fittingly projects into the seat 29 beneath the openings 28, the diameter of the seat 29 being equal to that of the bore 34. In this position, channel 42 is connected to the interior of the tube 14, but said passage is sealed against the head space 47. Also in this valve position, the sealing of the head space 47 against the environment is performed by the second seal 37 of the slide 35. In the operating position of the valve 20, the 3/2-way valve 22 is changed over to the operating connection A through which the supply of fluids into the interior of the vessel or the removal of the vessel content is possible.

In the case of the valve 20a connected to the gassing tube 13, the head 43 of the slide 35 is provided with a filter 24a which is connected to the duct 21a, said filter 24 serving simultaneously as a grip to move the slide 35.

In the duct 21 or 21a, there may be provided a means for length compensation in order to ensure that in each position, the slide is sealingly connected to the 3/2-way valve 22 or 22a.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A bioreactor comprising:

a sealable vessel having an outer wall and defining an interior head space, a valve extending through the outer wall of the sealable vessel, the valve including a valve chamber having a bore therein and a first aperture in communication with the interior head space, the bore having a first section and a second section and the first aperture being disposed substantially in the second section of the bore, the valve including a second aperture defined by the bore extending through an end portion of the second section, a slide displaceable between a first position and a second position in the bore of the valve chamber, the slide having an exterior surface and a substantially longitudinal channel extending through the slide, the slide having a slide end in which an opening of the longitudinal channel is provided, the slide and the first aperture being mutually configured so that the first aperture is closed by the slide when the slide is in the second position, a seat disposed substantially adjacent the first aperture of the valve chamber between the first aperture and the second aperture, the seat defining an enclosed space, the seat being positioned to engage the slide when the slide is in the second position, the enclosed space and the longitudinal channel being arranged to communicate through the opening of the longitudinal channel with the second aperture when the slide is in the second position, the second section of the bore defining at least a first portion and a second portion, the second portion having a larger cross section than the first portion, the second portion and the slide end being mutually configured to define therebetween an annular space, the interior head space being arranged to communicate by the annular space with the exterior surface of the slide and the first and second portions of the bore when the slide is in the first position, the longitudinal channel and the interior head space being arranged to communicate through the aperture and the opening of the longitudinal channel when the slide is in the first position, whereby vapor sterilization of the interior head space, the slide, the second section of the bore and the longitudinal channel is enabled when the slide is in the first position.

2. A bioreactor as defined in claim 1, wherein the slide further comprises:

a first seal, a second seal, an annular groove between the first seal and the second seal, the first seal contacting the bore of the valve chamber when the slide is in the first position and when the slide is in the second position, the second seal contacting the seat when the slide is in the second position.

3. A bioreactor as defined in claim 1 further comprising means for arresting the slide in the first position and means for arresting the slide in the second position.

4. A bioreactor as defined in claim 1 further comprising:

a multi-way valve disposed outside the sealable vessel, the multi-way valve having a condensate connection and an operating connection, a duct, and connection means for connecting the multi-way valve and the slide through the duct.

5. A bioreactor as defined in claim 4 further comprising:

a filter, the filter being mounted in the duct between the condensate connection and the valve.

6. A bioreactor as defined in claim 4, wherein the vessel further comprises a removable cover and the valve is mounted in the removable cover.

7. A bioreactor as defined in claim 4, further comprising automatic means for operating the valve automatically during a sterilization process.

8. A bioreactor comprising:

a sealable vessel having an outer wall and defining an interior head space, a valve extending through the outer wall of the sealable vessel, the valve including a valve chamber having a bore therein and a first aperture in communication with the interior head space, the bore having a first section and a second section and the first aperture being disposed substantially in the second section of the bore, the valve including a second aperture defined by the bore extending through an end portion of the second section, a slide displaceable between a first position and a second position in the bore of the valve chamber, the slide having a substantially longitudinal channel therein, the slide and the first aperture being mutually configured so that the first aperture is closed by the slide when the slide is in the second position, a seat disposed substantially adjacent the first aperture of the valve chamber between the first aperture and the second aperture, the seat being positioned to engage the slide when the slide is in the second position, the second section of the bore and the slide being mutually configured to defined therebetween an annular space, the interior head space being arranged to communicate by the annular space with the exterior surface of the slide and the second section of the bore when the slide is in the first position, a multi-way valve disposed outside the sealable vessel, the multi-way valve having a condensate connection and an operating connection, a duct, connection means for connecting the multi-way valve and the slide through the duct, a filter, the filter being mounted in the duct between the condensate connection and the valve, wherein the filter includes an outlet, and connection means for connecting the outlet of the filter to the slide, whereby the filter serves as a grip for displacing the slide.

* * * * *